US006475528B1

(12) United States Patent
Dietz

(10) Patent No.: US 6,475,528 B1
(45) Date of Patent: Nov. 5, 2002

(54) PREPARATION FOR REGENERATING COLLAGEN

(76) Inventor: Georg Dietz, Mauerkircher Str. 120, D-81925 Munich (DE)

( * ) Notice: Subject to any disclaimer, the term of this patent is extended or adjusted under 35 U.S.C. 154(b) by 0 days.

(21) Appl. No.: 09/673,359

(22) PCT Filed: Apr. 16, 1999

(86) PCT No.: PCT/EP99/02582

§ 371 (c)(1),
(2), (4) Date: Nov. 15, 2000

(87) PCT Pub. No.: WO99/53969

PCT Pub. Date: Oct. 28, 1999

(30) Foreign Application Priority Data

Apr. 16, 1998 (DE) .......................................... 198 16 934
Oct. 21, 1998 (DE) .......................................... 198 48 597

(51) Int. Cl.[7] .............................................. A01N 59/06
(52) U.S. Cl. ....................... 424/692; 424/693; 514/724; 514/738
(58) Field of Search ................ 424/600, 692, 424/693; 514/738, 724

(56) References Cited

U.S. PATENT DOCUMENTS 5,585,117 A    12/1996  Dietz .......................... 424/693

FOREIGN PATENT DOCUMENTS

| EP | 0 464 545 B1 | 11/1994 |
| JP | 53004394 | * 1/1978 |
| JP | 63044506 | * 2/1988 |
| WO | WO 93/24154 | 12/1993 |
| WO | WO 97/42269 | 11/1997 |

OTHER PUBLICATIONS

Patent Abstracts of Japan Publication No. 63044506A Published Feb. 25, 1988 and entitled "Dental Filling Agent Composition".

* cited by examiner

Primary Examiner—Alton Pryor
(74) Attorney, Agent, or Firm—Breiner & Breiner, L.L.C.

(57) ABSTRACT

A preparation which comprises calcium hydroxide, a dihydric or polyhydric alcohol and a fixed oil of vegetarian [sic] or animal origin and, where appropriate, pharmaceutically acceptable excipients; the production of a preparation of this type, the use of a preparation of this type for collagen regeneration and the use of a preparation of this type for producing a medicine for promoting collagen regeneration in vivo are described.

12 Claims, 5 Drawing Sheets

Figure 1:
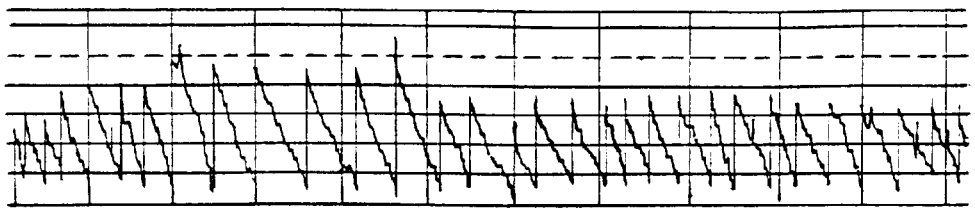

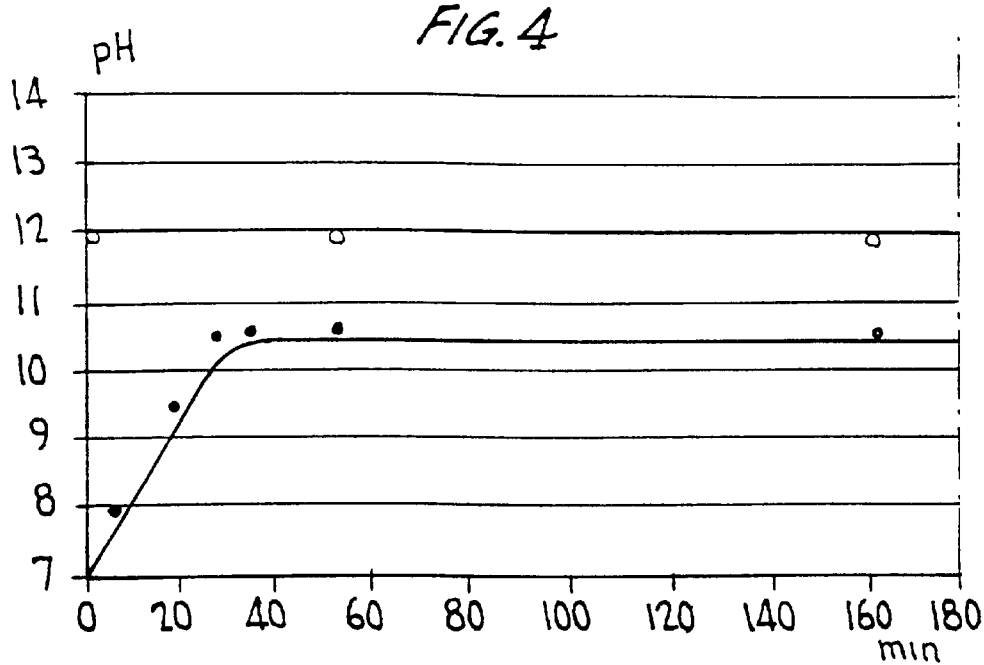
○ CALCIUM HYDROXIDE IN AQUEOUS SUSPENSION
● CALCIUM HYDROXIDE/GLYCEROL/NEATSFOOT OIL MIXTURE
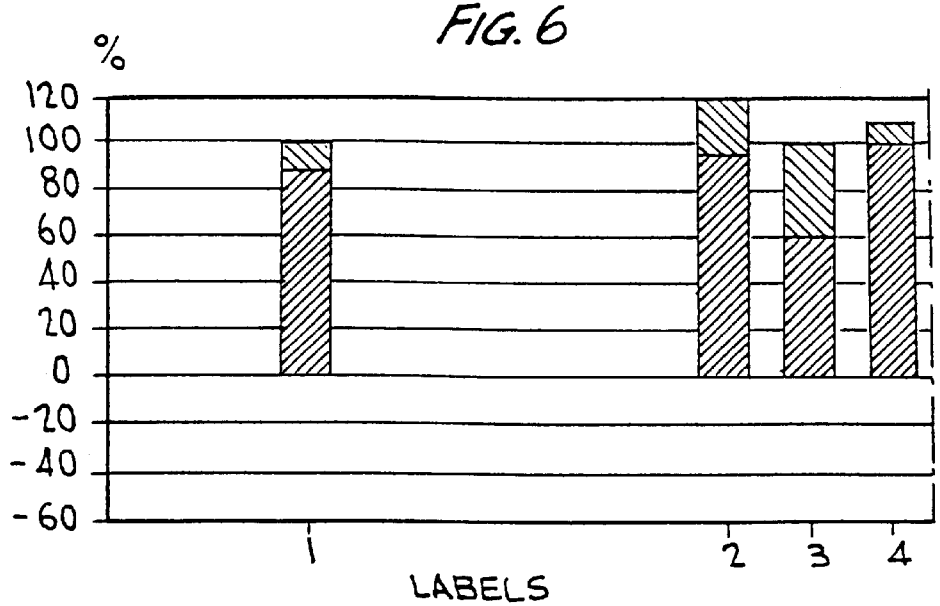
▨ CALCIUM HYDROXIDE/NEATSFOOT OIL
▨+▨ GLYCEROL/CALCIUM HYDROXIDE/NEATSFOOT OIL

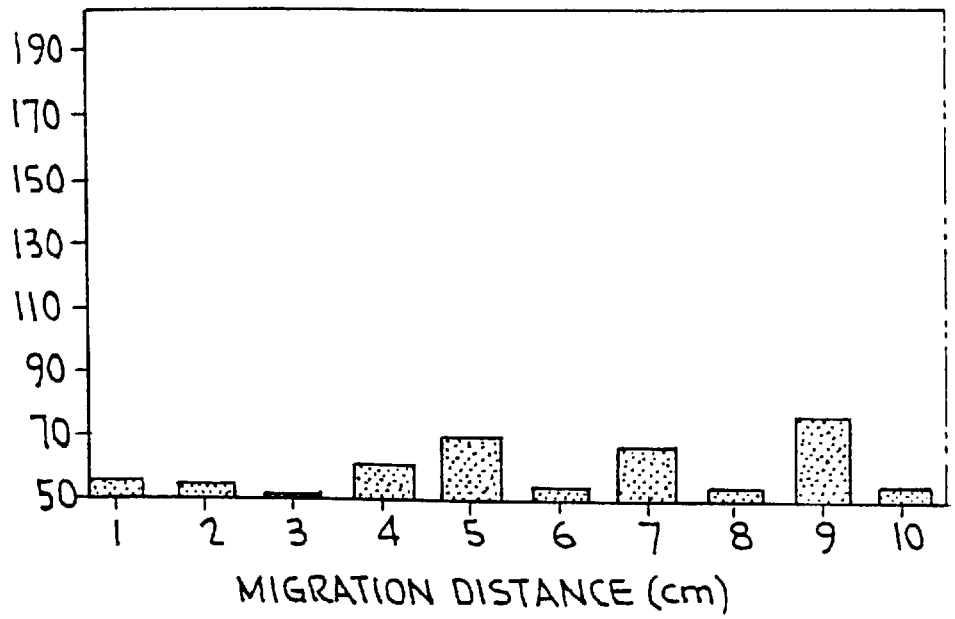
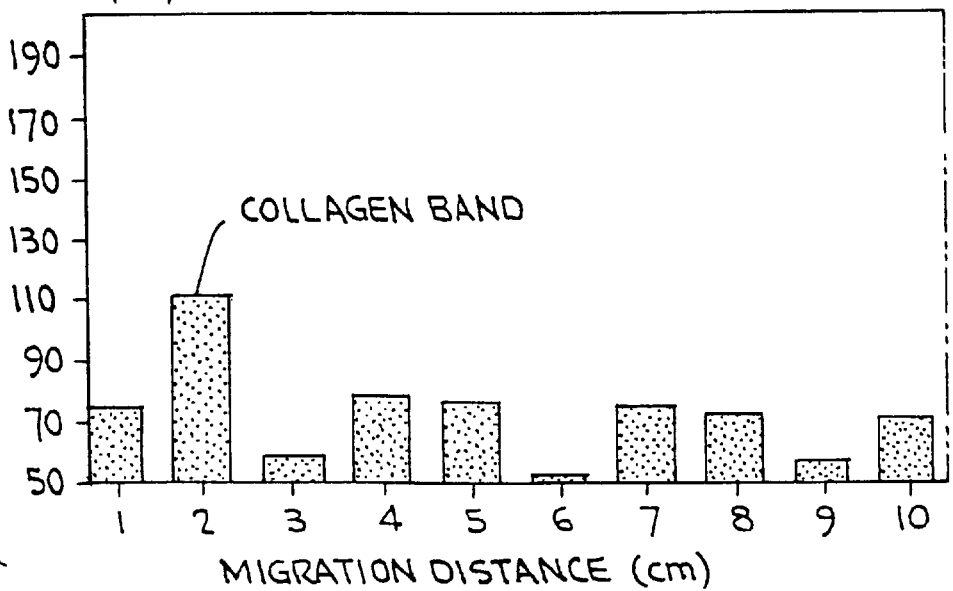
FIG. 5

CALCIUM HYDROXIDE / NEATSFOOT OIL

+ PROPYLENE GLYCOL / CALCIUM HYDROXIDE / NEATSFOOT OIL

CALCIUM HYDROXIDE / OLIVE OIL

+ GLYCEROL / CALCIUM HYDROXIDE / OLIVE OIL

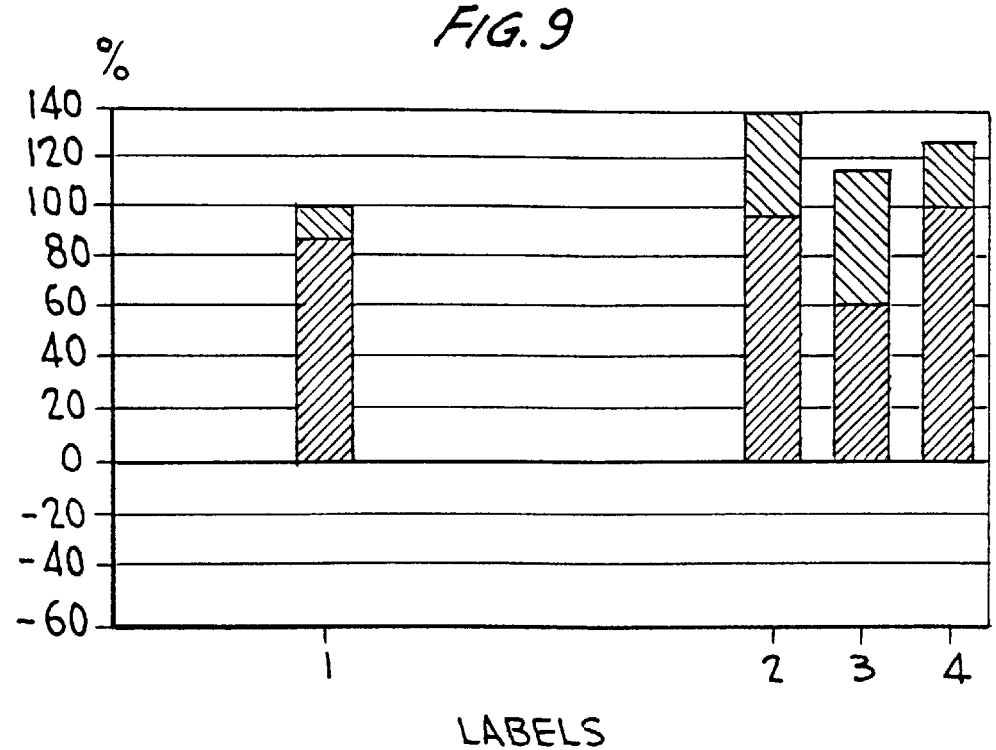

PREPARATION FOR REGENERATING COLLAGEN

This is a 371 of PCT/EP99/02582 filed Apr. 16, 1999.

The invention relates to a preparation composed of a fixed oil of vegetarian [sic] or animal origin, calcium hydroxide, a dihydric or polyhydric alcohol and, where appropriate, pharmaceutically acceptable excipients, to the preparation of a mixture of this type, to the use of a mixture of this type for collagen regeneration, and to the use of a mixture of this type for producing a medicine for promoting collagen regeneration in vivo.

Bone consists of about 60% mineral substance (hydroxyapatite, calcium phosphate) and about 40% organic material, principally collagen. Bone metabolism is determined mainly by the interplay of bone-constructing cells (osteoblasts) and bone-degrading cells (osteoclasts and osteocytes), whose activities in healthy bone are in a balanced relationship.

Bone formation can be divided into two main phases, (a) the synthesis of organic tissue (collagen synthesis) and (b) the deposition, which follows this and is mediated by so-called matrix vesicles, of mineral substance in the previously provided organic matrix.

The connective tissue protein collagen accounts for most of the organic substance in bone. The protein consists of three helically coiled polypeptide chains whose amino acid composition may vary, which leads to a diversity of individual types of collagen. It is common to all types of collagen that the collagen fibers have exceptionally great mechanical strength. This strength is based on a multiplicity of intra- and intermolecular linkages of the collagen fibers which, in this way, form the dense collagen fiber network of connective tissue. Bone tissue is—as already mentioned—formed by deposition of mineral substances (hydroxyapatite and calcium phosphate) in this network. Bone construction as a result of growth or regeneration processes is always preceded by collagen biosynthesis.

To date, in cases of bone injury of any cause, the bone regeneration process has been left to itself, at the most assisted by antibiotics and corticoids in order to prevent any risk of infection compromising the healing process.

Several factors able to influence bone formation and regeneration have also been described. These are mainly physical factors (mechanical and electrical forces), hormones (for example parathyroid hormone, calcitonin, insulin, glucocorticoids, 1,25-OHD3[sic]) and a not firmly defined group of growth factors with protein characteristics (osteochinin [sic], osteonectin, "insulin-like growth factors")—cf. S. Wallach, L. V. Avioli, J. H. Carstens jun. "Factors in Bone Formation", Calcified Tissue International 45: 4–6 (1989)). The effect of the hydrogen ion concentration (pH) on the metabolic processes in bone regeneration has not as yet been adequately investigated.

Dietz describes in DE-A-42 40 713 the use of a mixture of calcium hydroxide and neatsfoot oil for collagen regeneration following bone injuries. This preparation of calcium hydroxide and neatsfoot oil suffers, however, from the fact that its stability is very limited as a consequence of saponification. This may impair the effect of the mixture.

The invention was accordingly based on the object of indicating an improved mixture with long stability for the specific external influencing of the bone regeneration process through stimulation or initiation of collagen regeneration.

It has now surprisingly emerged that it is possible by using a preparation composed of calcium hydroxide, a dihydric or polyhydric alcohol and a fixed oil of vegetarian [sic] or animal origin and, where appropriate, pharmaceutically acceptable excipients to improve the stability of the preparation markedly and thus, on use of this preparation, in or for bone injuries, the extent of collagen regeneration in vivo is improved.

The present invention thus relates to preparations which comprise calcium hydroxide, a dihydric or polyhydric alcohol and a fixed oil of vegetarian [sic] or animal origin and, where appropriate, pharmaceutically acceptable excipients.

The present invention further relates to a process for producing a preparation of this type by means of mixing the calcium hydroxide and the dihydric or polyhydric alcohol and, where appropriate, pharmaceutically acceptable excipients into a fixed oil of vegetarian [sic] or animal origin.

The present invention further relates to the use of a preparation of this type for collagen regeneration.

The present invention further relates to the use of a preparation of this type for producing a medicine for promoting collagen regeneration in vivo.

Barium sulfate-containing mixtures of calcium hydroxide and neatsfoot oil have been used in dentistry as root-filling paste (DE-C 29 32 738). Mixtures of carboxylate cement, calcium hydroxide and neatsfoot oil have likewise been used in dentistry as temporary fixing means for provisional copings (DE-C 34 13 864). The task of the calcium hydroxide in the former case is to convert the acidic environment in the root canals into an alkaline one, resulting in the elimination of inflammations and gradual formation of a hard tissue barrier. In the latter case, the pulpitis-prophylactic effect of calcium hydroxide is utilized. The neatsfoot oil serves in both cases as a pasting auxiliary in order firstly to ensure simple and complete filling of the root canals with the actual active ingredient calcium hydroxide (and the contrast agent barium sulfate), and secondly to slow down the setting of the temporary fixing means for provisional copings so that the calcium hydroxide is also able to penetrate through the fine dentinal tubules to the pulp and display its effect there. Neither of the two references gives the slightest hint that the mixture according to the invention is able to induce extensive collagen regeneration as prerequisite for bone regeneration.

The term, which is novel according to the invention and is used hereinafter, "preparation" refers to a pharmaceutical preparation (sometimes also referred to as mixture hereinafter) which contains at least the abovementioned ingredients. It is particularly suitable for administration to humans or animals for research into collagen regeneration as prerequisite for bone regeneration.

The ingredients of the mixture according to the invention are described in more detail below:

The fixed oils of vegetarian [sic] origin which can be used may comprise one or more ingredients of the following vegetarian [sic] oils:

Soybean, sunflower, rape seed, cottonseed, linseed, castor, palm, palm kernel, coconut and olive oils.

The fixed vegetarian [sic] oils which can be used are preferably fixed vegetarian [sic] oils with high stability on heating, such as soybean, sunflower and olive oils, in particular olive oil.

The fixed animal oils which can be used may comprise one or more ingredients of the following animal oils:

Fish oils, animal foot oils and tallows.

The animal oils which can be used are preferably animal foot oils, in particular neatsfoot oil.

The dihydric or polyhydric alcohols which can be used may comprise dihydric alcohols such as ethylene glycol, propylene glycol, butylene glycol, pentylene glycol, hexylene glycol and polyethylene glycols such as diethylene glycol, triethylene glycol, polypropylene glycols such as dipropylene glycol, trihydric alcohols such as glycerol, tetrahydric alcohols such as threitol, erythritol, pentahydric alcohols such as arabitol, adonitol, xylitol, hexahydric alcohols such as sorbitol, mannitol, dulcitol, or higher polyhydric alcohols.

Preference is given to the use of dihydric and trihydric alcohols, such as ethylene glycol, propylene glycol, butylene glycol, pentylene glycol, hexylene glycol and polyethylene glycols such as diethylene glycol, triethylene glycol, polypropylene glycols such as dipropylene glycol, and trihydric alcohols such as glycerol, in particular glycerol as dihydric or polyhydric alcohol.

Without wishing to be bound to a theory, we assume that the dihydric or polyhydric alcohol prevents saponification of the vegetarian [sic] or animal fixed oil. This makes it possible to keep the mixture in a kneadable or creamy consistency for longer, so that collagen biosynthesis can be increased and improved.

A creamy, kneadable preparation is produced according to the invention from the individual ingredients. The calcium hydroxide is usually added to the preparation in amounts of 1–90% by weight, expediently 10–70% by weight, preferably 20–60% by weight, in each case based on the total weight of the preparation.

The fixed oil of vegetarian [sic] or animal origin is added to the composition to result in a creamy, kneadable consistency usually in amounts of 9–90% by weight, expediently 10–60% by weight, preferably 20–40% by weight, in each case based on the total weight of the preparation.

The dihydric or polyhydric alcohol is added to the composition to result in a creamy, kneadable consistency usually in amounts of 1–40% by weight, expediently 10–40% by weight, preferably 20–30% by weight, in each case based on the total weight of the preparation.

A preferred embodiment of the present invention relates to an abovementioned mixture which additionally comprises MgO. The MgO can be added for this purpose in amounts of 1–90% by weight, expediently 10–70% by weight, preferably 20–60% by weight, in each case based on the total weight of the preparation. However, it is assumed at present that MgO will preferably be added in smaller amounts of 10–20% by weight. MgO acts as an antacid in the bone material to counteract the acidic environment in the bone.

The ratio of calcium hydroxide to vegetarian [sic] or animal fixed oil in the mixture according to the invention can be 5/1 to 1/5, preferably 5/1 or 1/1. However, a deviation from the preferred mixing ratio may be necessary owing to the specific circumstances of the wound trauma.

If the mixture according to the invention is to have a particularly soft and smooth consistency, it is also possible to incorporate white petrolatum into it. It is usually possible to add white petrolatum in amounts of 1–60% by weight, expediently in amounts of 10–60% by weight, preferably in amounts of 20–40% by weight, in each case based on the total weight of the preparation.

Although it is not normally necessary to monitor the bone healing or regeneration process radiologically, this may nevertheless be indicated in some cases. In this case, it is also possible to incorporate barium sulfate as X-ray contrast agent into the mixture according to the invention. However, since the collagen regeneration resulting with barium sulfate is somewhat less good, the amount of barium sulfate added to the mixture according to the invention if necessary is just sufficient (for example 10–20% by weight based on the total weight of the preparation) for the mixture just to be radiographically visible.

Application of the mixture according to the invention onto or into the bone injury can take place—depending on its consistency—by use of syringes, spatulas or brushes.

There are numerous possible uses of the mixture according to the invention in general surgery and oral surgery, orthopedics, implantology, traumatology and the like, because the mixture according to the invention can be applied onto or into bone tissue injuries such as fracture surfaces, drillings, cavities and the like and immediately induces in vivo collagen regeneration at the particular site of application.

Since, as is well known, metallic fixing means are used in some relevant medical disciplines, it is advisable in this case to fill the drilling prepared for insertion of the fixing means with the mixture according to the invention before insertion of the fixing means, and only then to introduce the fixing means. It is possible in this way to counter the primary osteolysis unavoidable with such procedures and thus speed up the fitting or adaptation of the fixing means in or to the surrounding bone tissue and the fixing of the fixing means itself by the bone tissue.

Excess mixture moreover does not interfere in this case because on introduction of the fixing means into the drilling filled with the mixture either it is forced out again or diffuses into the spongiosa.

It ought to be self-evident that the mixture according to the invention and its ingredients must be both packaged and applied under sterile conditions.

It has also emerged in an extremely surprising manner that the mixture according to the invention counteracts, even without antibiotic and/or corticoid assistance, an inflammatory reaction caused by the bone injury, and rapidly causes it to subside. Its simple composition and pronounced efficacy for in vivo collagen regeneration with simultaneous inhibition of inflammation make the mixture according to the invention a composition which will be indispensable in future in bone traumatology.

The following examples are intended to illustrate the invention in detail.

EXAMPLE 1

A) It is firstly intended to elucidate the interaction between the mixture according to the invention and tissue. Thus, data on the distribution of the mixture according to the invention in bone tissue are the prerequisite for it to be possible to propose theories about a possible mechanism of action of the medicine. Experiments on tissue cultures are therefore more sensible than those on cell cultures because only in a tissue culture is it possible to study cell-cell interactions.

1. Material and Methods 1.1 Tissue Material

Human bone tissue resulting from osteotomies was made available by hospitals.

Embryonic bone tissue was obtained from 10–17-day old chicken embryos (Gallus domesticus).

1.2 Tissue Culture

The tissue was transferred into the transport medium immediately after removal. Bone fragments about 2 $mm^3$ in size were prepared under sterile conditions and, after determination of the weight, employed directly for the experiments.

Earl's modification of the minimal essential medium (MEM) Eagle with 20 mM Hepes buffer was used for the tissue culture.

Before the start of the experiment, 4% fetal calf serum and 1% antibiotic solution (penicillin/streptomycin/ amphotericin B) are added to the medium and, for the labeling experiments, additionally 1 mM beta-aminopropionidyl [sic], 2 mM Na ascorbate and 2 to 10 μg-isotopes (μC-proline [sic]). Cultivation is performed in 25 ml Erlenmeyer flasks at 37° C. in a shaking water bath at the lowest frequency.

1.3 Determination of the Respiratory Activity

The respiratory activity is a sensitive marker for the metabolic activity of the tissue. Even very small changes in the physiological condition of the tissue are reflected by a measurable change in the respiratory activity.

A Clark sensor (platinum/silver electrodes in saturated potassium chloride solution) was used to determine the respiratory activity. On application of a voltage of 0.8 V to the electrode, the oxygen reduction current is directly proportional to the oxygen partial pressure in the measured solution (culture medium). The supply of $O_2$-saturated medium where the oxygen partial pressure falls below a particular value, and the data analysis take place with computer control.

Bone tissue typically has a respiratory activity of 2–3 μl of $O_{2\times}min^{-1}\times g^{-1}$. The respiratory activity is thus in the region of the order of magnitude of the respiratory activity of resting muscle tissue. A typical respiratory curve for bone tissue is shown in FIG. 1. The sawtooth-like course of the respiratory curve shown in FIG. 1 derives from the fact that when the $O_2$ partial pressure in the measured solution falls below a particular value fresh $O_2$-saturated medium is supplied.

Figure 2:
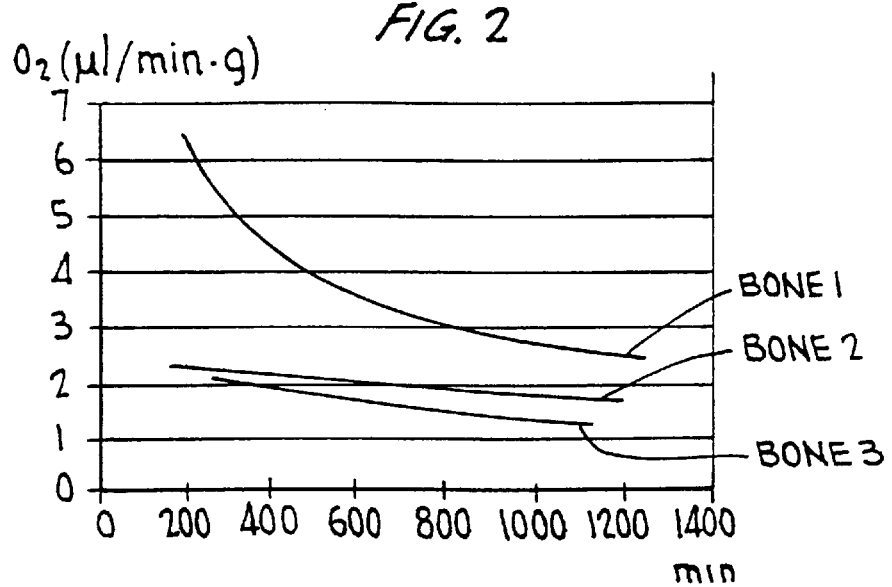

FIG. 2 shows average $O_2$ consumption values from three measurements. The oxygen consumption by embryonic bone tissue (Gallus domesticus) was determined in a tissue culture using the Clark sensor. The oxygen consumption is between 3 and 5 μl of $O^2$ [sic]$\times min^{-1}\times g^{-1}$ The respiratory activity falls by about 50% over the course of time, which is perfectly normal for tissue cultures.

1.4 Enzyme Assays

An enzyme which is thought to be closely connected with the mineralization of bone tissue is alkaline phosphatase. This enzyme was characterized some time ago but there is still discussion about the function of the enzyme in mineralization. Since there is a close connection between osteoblast activity and the activity of alkaline phosphatase it is possible to regard alkaline phosphatase as a marker of osteoblast activity. Elevated levels of alkaline phosphatase activity in blood serum are found during skeletal growth in childhood, during bone regeneration and in disorders of bone metabolism.

The activity of alkaline phosphatase was determined in a crude extract. For this purpose, 500 mg of tissue were mixed with 1 ml of disruption buffer and cut up with a knife. Subsequently 500 mg of grinding beads were added and disruption was carried out for 20 min. After centrifugation, the crude extract was employed for the measurements.

Alkaline phosphatase is detected on the basis of the conversion of p-nitrophenyl phosphate into nitrophenol and phosphate. The nitrophenol produced in the hydrolysis is yellow and can therefore be detected in a photometer at a wavelength of 410 nm.

Figure 3:
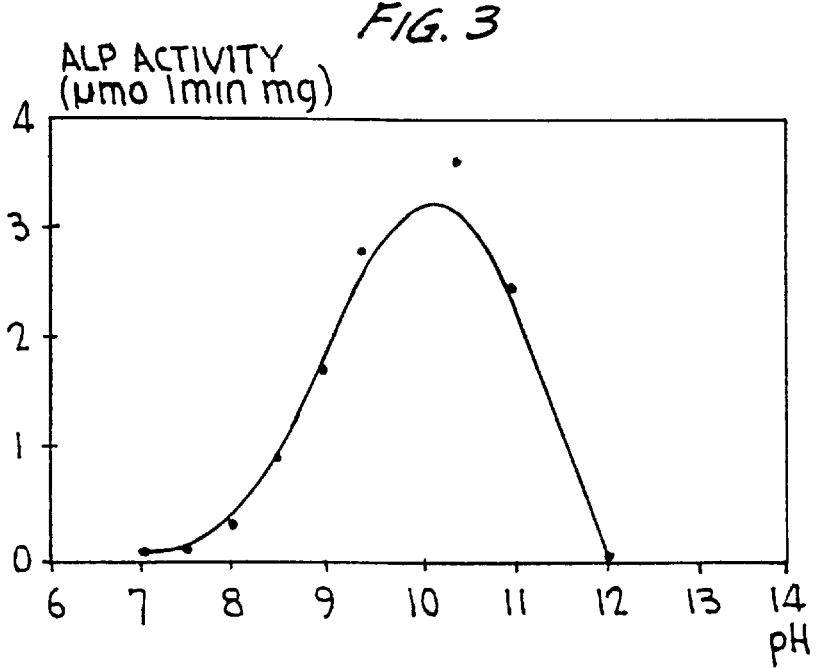

FIG. 3 shows the pH-dependence of the alkaline phosphatase activity. The activity of alkaline phosphatase from bone was determined on the basis of the conversion of p-nitrophenyl phosphate. The activity maximum is at pH 10.5. At the physiological pH of 7, alkaline phosphatase has only about 1% of the maximum activity.

1.5 pH Determination

A mixture according to the invention containing calcium hydroxide, glycerol and neatsfoot oil in the weight proportions 30% by weight, 30% by weight and 40% by weight, respectively, based on the total weight of the preparation, or an aqueous calcium hydroxide suspension was covered with 30 ml of imidazole/HCl buffer (1 mM, pH 7), after which the pH in the solution was continuously followed using a pH electrode.

It emerged from these measurements that a mixture of calcium hydroxide and glycerol in neatsfoot oil has fundamentally different properties from calcium hydroxide in aqueous suspension. FIG. 4 shows that an aqueous calcium hydroxide suspension causes an immediate pH jump to a pH 12, and that with the glycerol/calcium hydroxide/neatsfoot oil mixture according to the invention there is a slow rise as far as a pH above 10.

1.6 Collagen Determination

The major part of the organic substance in bone consists—as already mentioned—of collagen, a connective tissue protein. The bone growth and regeneration processes are associated with new collagen synthesis. The synthesis is followed by further intra- and extracellular collagen processes. It is possible by using radioactive collagen precursors ($^{14}$C-proline) to quantify accurately the rate of collagen synthesis in a tissue culture. This makes qualitative and quantitative recording of the effect of medicines on collagen synthesis possible.

The total collagen content is determined by the so-called hydroxyproline assay. The amino acid hydroxyproline occurs mainly in collagen, and the hydroxyproline content in other proteins can be neglected. After liberation of the amino acids from the proteins by hydrolysis, (16 h at 116° C., 22% HCl) and after chemical modification (oxidation of the 4-hydroxyproline to pyrrole), the total hydroxyproline content in the assay mixture is quantified by a specific color reaction with p-dimethylamino-benzaldehyde.

1.7 Determination of the Rate of Collagen Synthesis

Collagen in tissue and medium is obtained by Proff's (1991) modification of the method of Miller and Roths [sic] (c.f. E. J. Miller and R. H. Roths [sic] "Methods in symol [sic]." 82:33 (1982)). Via several precipitation steps with subsequent centrifugation, collagen is quantified by SDS gel electrophoresis and subsequent scintillation measurement (determination of the specific radioactivity). To calculate the rate of new synthesis, the collagen content determined through the incorporation of $^{14}$C-proline is related to the total collagen content determined by the hydroxyproline assay.

It is possible by quantifying the collagen biosynthesis to investigate the effect of calcium hydroxide products on bone formation.

Collagen biosynthesis is quantified—as indicated in 1.7—by the technique of radiolabeling of the collagen. One constituent of the collagen fiber is the amino acid proline. An exactly defined amount of $^{14}$C-labeled proline is added to the culture medium. This proline is incorporated into the proteins newly synthesized during incubation of the tissue. After separation of the collagen from other proteins it is possible, by determining the specific radioactivity, to make an accurate quantitative statement about the rate of new collagen synthesis.

The collagen is isolated by several precipitation steps with subsequent centrifugation and SDS gel electrophoresis. In the specific precipitation of the collagen, the collagen fibers are separated from other proteins by adjusting, by addition of sodium chloride, to a suitable salt concentration at which the non-collagen proteins mainly remain in solution but the collagen separates out of the solution as precipitate. The collagen is sedimented by subsequent centrifugation. In the SDS gel electrophoresis, proteins are separated from one another in a size-dependent manner. The proteins migrate in an electric field through a matrix of a highly crosslinked polymer (acrylamide). Small proteins migrate rapidly through this matrix because it affords less resistance to the small molecules, while large proteins migrate more slowly because their mobility is greatly impeded by the matrix. After staining, proteins are visible in this gel as so-called "bands". It is possible in this way to identify proteins on the basis of their size using internal size standards.

Proteins are made available for further analysis, for example radioactivity measurement, by cutting bands of interest out of the gel.

Extraction of Collagen

The tissue culture (cf. 1.2) was stopped by adding 3% acetic acid. Collagen which had dissolved was precipitated by 2 M sodium chloride at 4° C. overnight and then obtained by centrifugation (1 h, 24,000×g, 4° C.). The sediment was taken up in 10 ml of 3% strength acetic acid. Newly synthesized collagen present inside the tissue block was included in the analysis by mechanical disintegration of the tissue blocks. Tissue residues were obtained by centrifugation (1 h, 45,000×g, 4° C.). The sediment was fractionated by gel electrophoresis after solubilization. To check the fractionation of the proteins, they were stained in the gel.

The gel was cut up after the run into 5 mm-wide strips perpendicular to the direction of migration, and the gel fragments were transferred into scintillation vials and counted in a scintillation counter.

FIG. 5 shows the comparison between a vital and a heat-denatured tissue.

This comparison is depicted in FIG. 5 on the basis of the radioactivity distribution in the gel. Collagen is, as a relatively large protein, to be found in the region at a distance of 2 cm from the start.

The collagen band detectable through Coomassie staining can be assigned to a specific radioactive band.

FIG. 5 label I, head of femur, spongiosa, male, 45 years: Difference in collagen synthesis between vital and heat-denatured tissues (CPM: counts per minute). This shows the distribution of the radioactivity in the gel. The collagen band is located in a region at a distance about 2 cm from the start. A collagen band occurs only for vital tissue, which means that the radioactivity detectable in the gel corresponds to new collagen synthesis during the incubation.

The vital tissue shows a detectable collagen synthesis whereas the dead tissue no longer shows any metabolic activity. This shows that the detected radioactive collagen is in fact attributable to new collagen synthesis in the tissue culture and not to nonspecific binding of radioactive proline to proteins of the bone tissue. A comparable amount of tissue material was employed for all the experiments (about 100 mg).

Further radiolabeled bands of smaller size are detectable, possibly being collagen degradation products. Degradation of collagen in tissue culture is to be observed in particular in labeling experiments with an incubation time of more than 4 days. Radiolabeled proline is also present in the gel to a small extent, it not having been possible to remove this completely by the precipitations.

The tolerance of bone tissue to weakly alkaline pH 5 is evident from an experiment paralleling the experiment illustrated in FIG. 5. In the parallel experiment, the physiological Hepes buffer in the culture medium (pH 7.4) was replaced by a bicarbonate buffer (pH 8.0). It emerged from this that alkalinization of the culture medium to pH 8.0 resulted in no measurable difference in the collagen synthesis from pH 7.4. Above pH 8.5 there is no longer any increase in collagen regeneration relative to spontaneous collagen regeneration to be observed.

FIGS. 6 to 9 show the amount of newly synthesized collagen in the test batches with various mixtures according to the invention compared with control batches without this mixture or in the absence of a dihydric or polyhydric alcohol. The difference in the amount of newly synthesized collagen in the control and in the test batch is expressed in percent. 0% means that there is no increase in the amount of newly synthesized collagen compared with the control; 100% means collagen regeneration increased two-fold compared with the control under the influence of a mixture according to the invention.

It is evident from FIG. 6 that in four experiments collagen synthesis is increased by between 100 and 120% compared with the control under the influence of a glycerol/calcium hydroxide/neatsfoot oil mixture (composition: 30% by weight $Ca(OH)_2$, 30% by weight glycerol, 40% by weight neatsfoot oil). This increase is significant because experimental variations in collagen synthesis are in the range from 10 to 20%, whereas the increases determined under the influence of the glycerol/calcium hydroxide/neatsfoot oil mixture are between 100 and 120%. In addition, there is evidently also an increase in collagen synthesis, compared with a mixture containing no glycerol.

Figure 7:
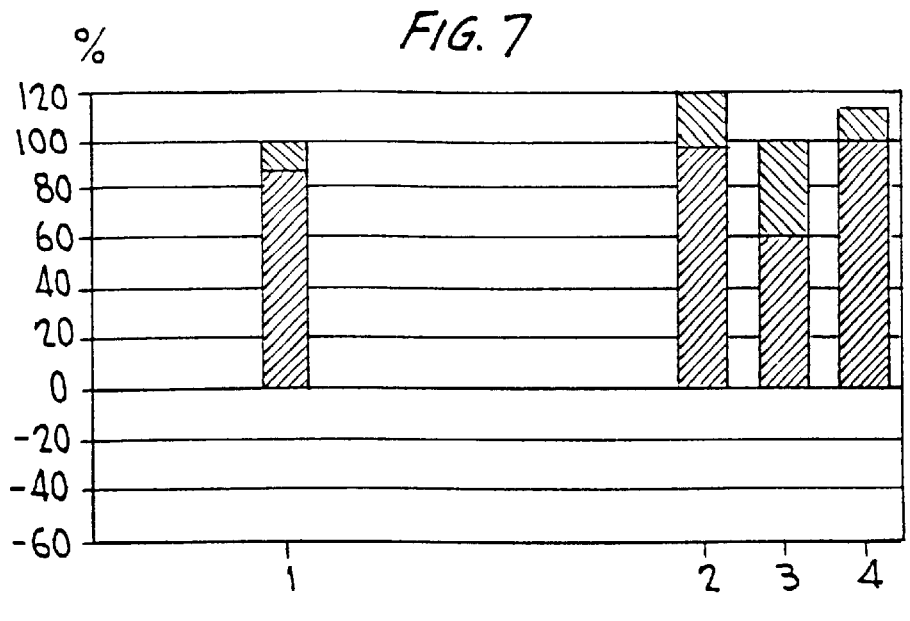

It is evident from FIG. 7 that in four experiments collagen synthesis is increased by between 100 and 120% compared with the control under the influence of a propylene glycol/calcium hydroxide/neatsfoot oil mixture (composition: 30% by weight $Ca(OH)_2$, 30% by weight propylene glycol, 40% by weight neatsfoot oil). This increase is significant because experimental variations in collagen synthesis are in the range from 10 to 20%, whereas the increases determined under the influence of the propylene glycol/calcium hydroxide/neatsfoot oil mixture are between 100 and 120%. In addition, there is evidently also an increase in collagen synthesis, compared with a mixture containing no propylene glycol.

Figure 8:
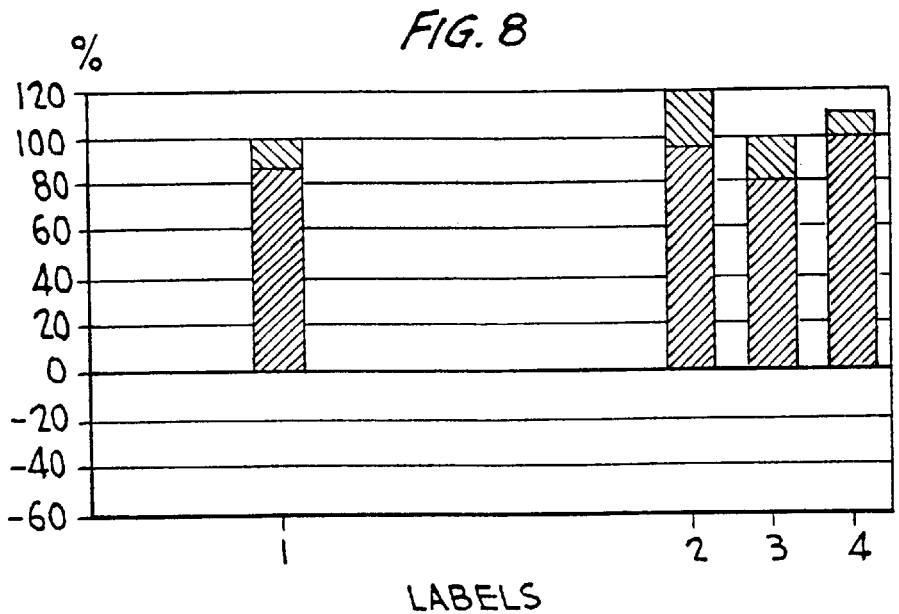

It is evident from FIG. 8 that in four experiments collagen synthesis is increased by between 100 and 120 [lacuna] compared with the control under the influence of a glycerol/calcium hydroxide/olive oil mixture (composition: 30% by weight $Ca(OH)_2$, 30% by weight glycerol, 40% by weight olive oil). This increase is significant because experimental variations in collagen synthesis are in the range from 10 to 20%, whereas the increases determined under the influence of the glycerol/calcium hydroxide/olive oil mixture are between 100 and 120%. In addition, there is evidently also an increase in collagen synthesis, compared with a mixture containing no glycerol.

It is evident from FIG. 9 that in four experiments collagen synthesis is increased by between 100 and 140% compared with the control under the influence of a glycerol/calcium hydroxide/magnesium oxide/neatsfoot oil mixture (composition: 20% by weight $Ca(OH)_2$, 20% by weight glycerol, 20% by weight magnesium oxide, 40% by weight neatsfoot oil). This increase is significant because experimental variations in collagen synthesis are in the range from 10 to 20%, whereas the increases determined under the influence of the glycerol/calcium hydroxide/magnesium oxide/neatsfoot oil mixture are between 100 and 140%. In addition, there is evidently also an increase in collagen synthesis, compared with a mixture containing no glycerol and MgO.

EXAMPLE 2

It was found in a stability test in which the mixtures indicated below were stored after formulation to a kneadable or creamy mass at room temperature and ambient humidity that retention of the desired consistency of the mixture can be extended by at least 50% of the stability period in the presence of a dihydric or polyhydric alcohol compared with samples without the alcohol.

Mixtures Used

1) Glycerol/calcium hydroxide/foot oil mixture (30% by weight/30% by weight/40% by weight) and
2) Propylene glycol/calcium hydroxide/neatsfoot oil mixture (30% by weight/30% by weight/40% by weight) and
3) Glycerol/calcium hydroxide/olive oil mixture (30% by weight/30% by weight/40% by weight)

| 1st mixture | without glycerol | with glycerol |
|---|---|---|
| kneadable consistency | 6 months | 12 months |
| creamy consistency | 12 months | 18 months |

| 2nd mixture | without propylene glycol | with propylene glycol |
|---|---|---|
| kneadable consistency | 6 months | 12 months |
| creamy consistency | 12 months | 18 months |
| 3rd mixture | without olive oil | with olive oil |
| kneadable consistency | 6 months | 12 months |
| creamy consistency | 12 months | 18 months |

What is claimed is:

1. A pharmaceutical preparation comprising consisting essentially of calcium hydroxide, a fixed oil of vegetable or animal origin, a dihydric or polyhydric alcohol, and, optionally pharmaceutically acceptable excipients, barium sulfate, white petrolatum, and magnesium oxide and mixtures thereof in absence of a resin.

2. The pharmaceutical preparation of claim 1, wherein the ratio by volume of calcium hydroxide and the fixed oil is 5/1 to 1/5.

3. The pharmaceutical preparation of claim 1 wherein the ratio by volume of calcium hydroxide and the fixed oil is 1/1.

4. The pharmaceutical preparation of claim 1, wherein the ratio by volume of calcium hydroxide and the fixed oil is 5/1.

5. The pharmaceutical preparation of claim 1 wherein said barium sulfate is present.

6. The pharmaceutical preparation of claim 1 wherein said white petrolatum is present.

7. The pharmaceutical preparation of claim 1 wherein said MgO is present.

8. The pharmaceutical preparation of claim 1, wherein said dihydric or polyhydric alcohol is glycerol.

9. The pharmaceutical preparation of claim 1, wherein said fixed oil is neatsfoot oil.

10. The pharmaceutical preparation of claim 1, wherein said fixed oil is olive oil.

11. A process for producing the pharmaceutical preparation of any one of claims 1 to 10 consisting essentially of mixing said calcium hydroxide, the dihydric or polyhydric alcohol, the fixed oil said optional pharmaceutically acceptable excipients, barium sulfate, white petrolatum, and magnesium oxide and mixtures thereof to provide a composition of kneadable and creamy consistency.

12. A method of regenerating collagen in bone tissue comprising applying to bone tissue the pharmaceutical preparation of any one of claims 1 to 10.

* * * * *

UNITED STATES PATENT AND TRADEMARK OFFICE
CERTIFICATE OF CORRECTION

PATENT NO.    : 6,475,528 B1
DATED         : November 5, 2002
INVENTOR(S)   : Georg Dietz It is certified that error appears in the above-identified patent and that said Letters Patent is hereby corrected as shown below:

Column 5,
Line 21, "$O_{2x}min^{-1}xg^{-1}$" should read -- $O_2 \times min^{-1} \times g^{-1}$ --.

Column 9,
Lines 16-32, the tables as follows

"

| 1st mixture | without glycerol | with glycerol |
|---|---|---|
| kneadable consistency | 6 months | 12 months |
| creamy consistency | 12 months | 18 months |

| 2nd mixture | without propylene glycol | with propylene glycol |
|---|---|---|
| kneadable consistency | 6 months | 12 months |
| creamy consistency | 12 months | 18 months |
| 3rd mixture | without olive oil | with olive oil |
| kneadable consistency | 6 months | 12 months |
| creamy consistency | 12 months | 18 months |

" should read

--

| 1st mixture | without glycerol | with glycerol |
|---|---|---|
| kneadable consistency | 6 months | 12 months |
| creamy consistency | 12 months | 18 months |

| 2nd mixture | without propylene glycol | with propylene glycol |
|---|---|---|
| kneadable consistency | 6 months | 12 months |
| creamy consistency | 12 months | 18 months |

| 3rd mixture | without olive oil | with olive oil |
|---|---|---|
| kneadable consistency | 6 months | 12 months |
| creamy consistency | 12 months | 18 months |

--.

UNITED STATES PATENT AND TRADEMARK OFFICE
CERTIFICATE OF CORRECTION

PATENT NO. : 6,475,528 B1
DATED : November 5, 2002
INVENTOR(S) : Georg Dietz

It is certified that error appears in the above-identified patent and that said Letters Patent is hereby corrected as shown below:

Column 9,
Line 34, "comprising consisting" should read -- consisting --.

Column 10,
Line 28, "oil said" should read -- oil, said --.

Signed and Sealed this

Twenty-ninth Day of April, 2003

JAMES E. ROGAN
*Director of the United States Patent and Trademark Office*